(12) United States Patent
Bakeev et al.

(10) Patent No.: US 6,451,892 B1
(45) Date of Patent: *Sep. 17, 2002

(54) METHOD FOR PREVENTING OR RETARDING THE FORMATION OF GAS HYDRATES

(75) Inventors: Kirill N. Bakeev, Ringwood, NJ (US); Kevin Harris, Middlesex (GB); Carl B. Argo, Surrey (GB); Michael A. Drzewinski, Long Valley, NJ (US); David E. Graham, Long Valley, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/351,900

(22) Filed: Jul. 13, 1999

(51) Int. Cl.$^7$ .............................. C08K 5/05; C08K 5/06
(52) U.S. Cl. ............................. 524/386; 137/3; 137/13; 524/376; 524/389; 524/612; 524/761; 524/765; 524/767; 585/15; 585/950; 526/264

(58) Field of Search .................................. 524/548, 761, 524/765, 767, 386, 376, 389, 612; 526/264; 137/3, 13; 585/15, 950

(56) References Cited

U.S. PATENT DOCUMENTS

| | | | | |
|---|---|---|---|---|
| 5,723,524 A | * | 3/1998 | Cohen et al. | 524/376 |
| 5,874,660 A | * | 2/1999 | Colle et al. | 585/15 |
| 5,880,319 A | * | 3/1999 | Sloan, Jr. | 585/15 |
| 6,028,233 A | * | 2/2000 | Colle et al. | 585/15 |
| 6,117,929 A | * | 9/2000 | Bakeev et al. | 52/376 |

* cited by examiner

*Primary Examiner*—Judy M. Reddick
(74) *Attorney, Agent, or Firm*—Walter Katz; William J. Davis; Marilyn J. Maue

(57) ABSTRACT

A composition for preventing or retarding the formation of gas hydrates during the transport of a fluid comprising water and a hydrocarbon through a conduit. The composition is a homopolymer of vinyl caprolactam, or copolymers thereof, having a low molecular weight in the range of 500 to 2500, which is made in a polymerization solvent, preferably a glycol ether, most preferably 2-butoxyethanol and also including a carrier solvent, preferably monoethylene glycol.

7 Claims, No Drawings

METHOD FOR PREVENTING OR RETARDING THE FORMATION OF GAS HYDRATES

CROSS-REFERENCE TO RELATED U.S. PATENT APPLICATIONS

This application is related to co-pending U.S. patent application, Ser. No. 09/204,768, filed Dec. 3, 1998, now U.S. Pat. No. 6,117,299 which describes the preparation of an inhibitor composition by polymerizing vinyl caprolactam in 2-butoxyethanol solvent.

BACKGROUND OF THE INVENTION

1. Field of the Invention

The invention relates to a method for preventing or retarding the formation of gas hydrates, or for reducing the tendency of such hydrates to agglomerate, during the transport of a fluid comprising water and a hydrocarbon through a conduit, and, more particularly, to the addition to the fluid of a composition of a low molecular weight vinyl caprolactam polymer, or copolymers thereof, which is made in a polymerization solvent, and including a carrier solvent different from said polymerization solvent, to inhibit such gas hydrate formation.

2. Description of the Prior Art

It is well known in the art that the formation of gas hydrates in a conduit, e.g. in a pipeline, where an aqueous phase is inherently present, during the transport of liquids such as oil, and of gases, particularly lower hydrocarbons, e.g. methane, ethane, propane, butane, isobutane and natural gas, is a serious problem, especially in areas with a low temperature in the winter season or in the sea. Generally, the ambient temperatures in such areas are so low that gas hydrates are formed in the gas transportation pipeline, due to the inevitable presence of co-produced water therein. Insulation of the pipelines may decrease the opportunity for gas hydrate formation; however, if the field is relatively small and some distance from the production facilities, the cost of providing suitable insulation is too high to make such a field economically attractive. It is also known to add anti-freeze compounds, for example, ethylene glycol or methanol, during transport of such liquids and gases to minimize gas hydrate formation; however, large quantities of these highly flammable compounds are required to be effective which is expensive and unsafe.

Representative of the prior art in this field are U.S. Pat. Nos. 4,915,176; 5,420,370; 5,432,292; and 5,723,524; EPO 0323774A1; EPA 0457375A1; EPA 0526929A1; Can. Pat. Appln. 2,073,577; "Gas Hydrates and Hydrate Prevention", 73 GPA Annual Convention, pages 85–93; WO 96/08456; WO 96/08636; WO 93/25798; WO 94/12761; WO 95/17579; and WO 95/32356.

Representative of such art is the disclosure in U.S. Pat. No. 5,723,524 that poly(vinyl caprolactam) (PVCL), synthesized in isopropanol, and having an average molecular weight of 36,000 amu, as determined by gel permeation chromatography (GPC), using polyethylene glycol as standard, is a gas hydrate inhibitor.

Accordingly, it is an object of this invention to provide an improved composition and method for retarding the formation of gas hydrate in a hydrocarbon gas pipeline.

SUMMARY OF THE INVENTION

What is described herein is a composition for effectively preventing or retarding the formation of gas hydrates, or for reducing the tendency of gas hydrates to agglomerate, during the transport of a fluid comprising water and a hydrocarbon, through a conduit. The composition comprises a vinyl caprolactam homopolymer (PVCL), or copolymers thereof, preferably copolymers with vinyl pyrrolidone (VP), having a low molecular weight of about 500 to about 2500, preferably 750–1500, which are made in a polymerization solvent which is a glycol ether, containing an alkoxy group having at least 3 carbon atoms, and most preferably, 2-butoxyethanol (BGE), and includes a carrier solvent different from the polymerization solvent, preferably, monoethylene glycol (MEG).

DETAILED DESCRIPTION OF THE INVENTION

The polymer which exhibits advantageous inhibitory characteristics in the composition of the invention is a homopolymer of vinyl caprolactam, or copolymer thereof, having a molecular weight of about 500 to about 2500, preferably 750–1500, as determined by GPC using polyethylene glycol as the standard.

The composition of the invention may also include low molecular weight copolymers of vinyl caprolactam with one or more monomers selected from N-vinylpyrrolidone; acrylamide; N-alkyl acrylamides, e.g. N,N-dimethyl acrylamide; N-[1-(2-pyrrolidonylethyl)] acrylamide; N,N-dialkyl aminoalkyl methacrylamide, e.g. N,N-dimethylamino propyl methacrylamide; N,N-dialkyl aminoalkyl (meth)acrylates; e.g. N,N-dimethylaminoethyl (meth)acrylate and quaternized salts thereof, including N-alkyl halides and the like. The homopolymer of vinylcaprolactam, and copolymers with vinylpyrrolidone monomer, are preferred.

Generally, the polymer solution used in the composition of the invention is present in an amount of about 30 to 60%, preferably 45 to 55%, by weight in admixture with the solvent. The polymer inhibition concentration in the pipeline, i.e. in the aqueous phase, water being inherently present therein, is about 0.1 to 3%, preferably 0.5–1%, by weight. The solvent* inhibition concentration, accordingly, is about 1 to 9% by weight of the aqueous phase.

* total of all solvents present in the composition

The polymer is synthesized from its monomer, or monomers, in a polymerization solvent which preferably is a glycol ether containing an alkoxy group having at least 3 carbon atoms. Representative of such suitable glycol ethers are 2-butoxyethanol (ethylene glycol monobutyl ether); propylene glycol butyl ether; (diethylene glycol) monobutyl ether; and 2-isopropoxy-ethanol. 2-Butoxyethanol (BGE) is most preferred.

The product of the polymerization is a composition of the polymer, e.g. poly(vinyl caprolactam) (PVCAP), in the polymerization solvent, e.g. BGE. Generally, the weight ratio of the polymerization solvent to the polymer is about 1:1.5 to 3:3 to 1, preferably about 1.5:1.

The composition is then provided with a suitable carrier solvent such as monoethylene glycol (MEG), methanol, ethanol, propanol, 1,4-butanediol, butanol, pentanol, hexanol, cyclohexyl pyrrolidone, propargyl alcohol, N-methylpyrrolidone and the like, preferably MEG. Preferably the concentration of MEG in the aqueous phase, i.e. under pipeline inhibition conditions, is about 2.5–10 wt. %, most preferably 4–5 wt. %.

The thus-formed solution with carrier solvent can be further diluted with a dilution liquid, preferably water or methanol, or mixtures thereof, if desired, to form a use composition for injection into the pipeline. Suitable inhibitor composition to dilution liquid is 0.5:1 to 5:1, preferably about 1:1.

The following examples are provided to illustrate the invention.

A. General Method

The gas hydrate inhibition tests were conducted in a 500 ml, 316 stainless steel autoclave vessel having a usable volume of 200 ml, equipped with a thermostated cooling jacket, sapphire window, inlet and outlet, platinum resistance thermometer (PRT) and magnetic stirring pellet. The rig is rated up to 400° C. and down to −25° C. Temperature and pressure are data logged, while the cell content is visually monitored by a boroscope video camera connected to a time lapsed video recorder. Hydrate formation in the rig is detected using a combination of three methods: visual detection of hydrate crystals, decrease in vessel pressure due to gas uptake and by the temperature exotherm created by heat released during hydrate formation.

The rig was cleaned prior to running a blank and/or test solutions. An air drill with wet and dry emery paper was used to remove traces of any adsorbed chemicals therein with a small amount of water being added to the rig. The vessel was then rinsed several times with double distilled water. A blank solution of 200 ml of double distilled water was run to confirm the reproducibility of the test. Formation of hydrates within 5–15 minutes was taken as a standard time for a given set of testing conditions, e.g. Ravenspurn gas, 85 bar and T=5° C.

A Ravenspurn synthetic gas mixture (Southern North Sea) having the following composition was used for hydrate testing:

| Ravenspurn Synthetic Gas | |
|---|---|
| Component | Mol % |
| $CO_2$ | 1.0 |
| Methane | 95.31 |
| Ethane | 2.96 |
| Propane | 0.53 |
| Iso-Butane | 0.1 |
| n-Butane | 0.1 |

B. Experimental Procedure for Evaluation of Hydrate Inhibitors

Pipeline conditions were simulated by placing 100–200 ml of the use polymer solution (with total polymer concentration in the aqueous phase equal to about 1 wt. %) into a vessel fitted with a PTFE stirrer pellet. The rig top of the vessel was replaced and the securing ring tightened. A boroscope and video camera were then attached to the apparatus. The rig was then stirred and allowed to cool to a required temperature. Upon reaching the pre-set temperature, the stirrer was stopped and the video recorder and computer data logger started. The rig was then charged with Ravenspurn gas to reach the required pressure. A slightly higher pressure (2–3 bars) was used to allow for some gas dissolution in the water and the slight drop in pressure as the gas cooled. The stirrer was started at 500 rpm and the temperature (40° C. or 5° C.), pressure (85 bar) and start time ($t_o$) recorded. The run was terminated upon the formation of hydrates, usually at the moment of a pressure drop, which might or might not follow the exotherm, and visual hydrate formation, if a large amount of hydrates was formed and the amplitude of the effect. The final temperature, pressure and time (t) of hydrate formation was noted.

The onset of the hydrate formation time (t−$t_o$ mins) is indicated in the examples given below. The number of a given test rig also is indicated in the brackets [ ] next to the hydrate formation time. Normally, a test was considered to be a pass (success) if no hydrate formation was observed within 48 hours. Some tests were terminated before 48 hours even when no hydrate formation was noted in the rig. The relative efficiencies of the inhibiting polymers are thus proportional to the measured induction times.

Since the equilibrium melting temperature for hydrate decomposition for the Ravenspurn gas in double distilled water and P=85 bar is about 15.50° C., the hydrate subcooling is equal to 10.5° C. (T=5° C. is the temperature of the measurements); or 11.50° C. at P=85 bar, T=4° C.

C. Experimental Runs Preparation of Inhibitor Compositions

Examples 1–3 below illustrate the direct preparation of low molecular weight poly(vinyl caprolactam) (PVCL) in 2-butoxyethanol (BGE).

EXAMPLE 1

300 g. of 2-butoxyethanol was charged into a 1-liter resin reaction fitted with a propeller agitator, reflux condenser, nitrogen inlet tube and thermowatch, and heated to 150° C. A monomer pre-mix was prepared by mixing 200 g of vinyl caprolactam with 4.00 g of di-t-butyl peroxide initiator in a 400-ml beaker. Then the monomer pre-mix was pumped into the reaction kettle over a period of 2 hours. The reaction mixture was held at 150° C. for 1.5 hours before adding 0.50 g of di-t-butyl peroxide initiator, and then held at 150° C. for an additional 3 hours. Upon cooling to room temperature, the product obtained was a light brown, viscous poly(vinyl caprolactam) homopolymer in 2-butoxyethanol at 40% solids. Residual vinyl caprolactam present was only 0.9%, as determined by GC analysis. The PVCL polymer had a relative viscosity of 1.074 (1% in 2-butoxyethanol), a GPC molecular weight of 1,210 (polyethylene glycol standard), and a cloud point of 42° C.

EXAMPLE 2

The procedure of Example 1 was followed except that two booster initiators were added twice every 1.5 hours. A light brown, viscous poly(vinyl caprolactam) homopolymer in 2-butoxyethanol at 40% solids was obtained after cooling to room temperature. Residual vinyl caprolactam was 0.6%. The PVCL polymer had a relative viscosity of 1.064, a GPC molecular weight of 780, and a cloud point of 41° C.

EXAMPLE 3

The procedure of Example 1 was followed except that the reaction was performed at 145° C. and two booster initiators were added twice every 1.5 hours. Light brown, viscous poly(vinyl caprolactam) in 2-butoxyethanol at 40% solids was obtained after cooling to room temperature. Residual vinyl caprolactam was 0.25% by GC analysis. The PVCL polymer had a relative viscosity of 1.082, a GPC molecular weight of 1,310, and a cloud point of 42° C.

EXAMPLE 4

Example 4 below illustrates the preparation of a low molecular weight copolymer of vinyl caprolactam (VCL) and vinyl pyrrolidone (VP) (75/25 wt. ratio) in 2-butoxyethanol.

300 g. of 2-butoxyethanol was charged into a 1-liter resin kettle fitted with a propeller agitator, reflux condenser, nitrogen inlet tube, and thermowatch. The reactor was heated to 150° C. and maintained at that temperature throughout the run. A monomer pre-mix was prepared by mixing 150.0 g. of vinyl caprolactam, 50.0 g. of vinyl pyrrolidone and 4.00 g. of di-t-butyl peroxide initiator (Luperox D1, 95% liquid; Elf Atochem) in a 400-ml beaker. The monomer pre-mix was pumped into the kettle over a period of 2 hours. The reaction mixture was then held at 150° C. for 1.5 hours. Thereafter 0.50 g. of di-t-butyl peroxide was added and the reaction was held at 150° C. for an additional 3 hours. At the end of the reaction, a light brown, viscous poly(vinyl caprolactam) in 2-butoxyethanol at 40% solids was obtained upon cooling to room temperature. Residual vinyl caprolactam and vinyl pyrrolidone were 0.097% and 0.022%, respectively. The copolymer has a relative viscosity of 1.094, a GPC molecular weight of 2,080, and a cloud point of 55° C.

D. Gas Hydrate Inhibition Testing

Examples 5–8 illustrate the effectiveness of the compositions of the invention to inhibit gas hydrate formation in a hydrocarbon fluid

EXAMPLE 5

The compositions of Examples 1–3, prepared at 50 wt. % PVCAP in BGE, were tested under the experimental conditions of [MEG]=5.4 wt %; [BGE]=1.5 wt %; [PVCAP]=1.0 wt %; fluid phase composition: saline water/gas condensate ratio=1:1 vol/vol, and [NaCl]=1.0 wt %; and at P=85 bar, T=5° C., which corresponds to 10.5° C. of operating subcooling.

In this experiment, there were 8 passes out of 10 runs (i.e. no hydrate formation for >47 hours), with only 2 failures after 15 and 38 hours of test. The successful runs were evidenced by a small pressure drop (1–2 bars) and no exotherms, thus indicating high inhibition efficiency of the tested formulation at the above sub-cooling. The times for the onset of gas hydrate formation ($t-t_o$ min) were as follows:

| | |
|---|---|
| >2863 min [6]* | >2839 min [1] |
| >2863 min [5] | >2842 min [2] |
| >2870 min [3] | >2840 min [7] |
| >2868 min [4] | >4015 min [9] |
| >927 min [9] | 2315 [1] |

*brackets indicate a given rig number

EXAMPLE 6

Example 6 is an actual field trial to illustrate the effectiveness of the compositions of the invention to inhibit gas hydrate formation in natural gas pipelines.

The inhibitor composition given below in an amount of 3–3.5 l/day was co-injected with 3–3.5 l/day of methanol into a commercial natural gas pipeline containing 11–13% hydrogen sulfide at P=550 psi at the injection point dropping to 250 psi along the line, a length of 8–9 miles. The produced gas volume was $160 \times 10^3$ m$^3$/day. The produced condensate was 3 m$^3$/day.

| Inhibitor Composition | Wt. % |
|---|---|
| Polymer of Ex. 1 (at 50 wt % PVCAP in BGE) | 10.14 |
| MEG | 50.67 |
| BGE | 17.32 |
| Water | 21.87 |
| Total: | 100.00 |

No hydrate formation was observed during continuous operation of the pipeline, and, it was believed further reduction in the chemical dose level used can optimize these results.

EXAMPLE 7

An experiment was carried out with a polymer (the same as in Example 5) in the following conditions:

[MEG]=4.17 wt %
[BGE]=1.5 wt %
[PVCAP]=1.0 wt %
[condensate]/[saline water]=1:1 v/v
[NaCl]=1.0 wt %
P=85 Bar, T=4° C. which corresponds to 11.5° C. of operating sub-cooling In this experiment, 4 passes out of 5 runs, i.e. no hydrate formation for >47 hours, resulted, with one failure observed after about 20 hours, and characterized by a small pressure drop (1–2 bars) and no exotherm, thus indicating high inhibition efficiency of the tested formulation at the above sub-cooling.

The times obtained from different rigs of similar design for the onset of gas hydrate formation ($t-t_o$ min) were as follows: >4019 min [0]; 3846 min [1]; 1249 min [2]; 4023 min [7]; and 4023 min [8].

E. Comparative Run

EXAMPLE 8

(Control)

A control experiment was run with the following composition:

[MEG]=5.4 wt %
[condensate]/[saline water]=1:1 v/v
[BGE]=1.5 wt %
[NaCl]=1.0 wt %
No polymer was added
P=85 Bar/T=5° C.; 10.5° C. of operating sub-cooling Gas hydrates were formed within the average induction time of about 11 minutes, as shown below:

5 min [8] 5 min [3] 8 min [5] 14 min [4] 21 min [6], and hydrate formation proceeds catastrophically with a sharp decrease in pressure and large exotherms.

While the invention has been described with particular reference to certain embodiments thereof, it will be understood that changes and modifications may be made which are within the skill of the art. Accordingly, it is intended to be bound only by the following claims, in which:

What is claimed is:

1. A composition for preventing or retarding the formation of gas hydrates or for reducing the tendency of gas hydrates to agglomerate, during the transport of a fluid comprising water and a hydrocarbon, through a conduit, where an aqueous phase is inherently present, comprising, (a) a solution of a homopolymer of vinyl caprolactam, or copolymer thereof, having a molecular weight in the range of about 500 to about 2500, (GPC, polyethylene glycol standard), which homopolymer or copolymer is sythesized in (b) a polymerization solvent which is a glycol ether containing an alkoxy group having at least 3 carbon atoms, and (c) a carrier solvent, and, optionally, (d) water or methanol, or mixtures thereof.

2. A composition according to claim 1 wherein (c) is monoethylene glycol.

3. A composition according to claim 1 wherein the weight ratio of polymerization solvent (b): vinyl caprolactam homo- or copolymer (a) is about 1:1.5 to about 3.3:1.

4. A composition according to claim 1 wherein said polymerization solvent is 2-butoxyethanol.

5. A composition according to claim 1 wherein said molecular weight is about 750 to about 1500.

6. A composition according to claim 1 wherein (a) comprises about 30–60 wt. % based on (a)+(b).

7. A composition according to claim 6 wherein (a) comprises 45–55 wt. % based on (a)+(b).

* * * * *